US010339719B2

(12) United States Patent
Jagga et al.

(10) Patent No.: US 10,339,719 B2
(45) Date of Patent: *Jul. 2, 2019

(54) SYSTEM AND METHOD FOR PROJECTED TOOL TRAJECTORIES FOR SURGICAL NAVIGATION SYSTEMS

(71) Applicant: SYNAPTIVE MEDICAL (BARBADOS) INC, Bridgetown (BB)

(72) Inventors: Victor Jagga, Mississauga (CA); Michael Wood, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/995,371

(22) Filed: Jun. 1, 2018

(65) Prior Publication Data
US 2018/0286135 A1    Oct. 4, 2018

Related U.S. Application Data

(63) Continuation of application No. 15/125,399, filed as application No. PCT/CA2014/050767 on Aug. 12, (Continued)

(51) Int. Cl.
*G06T 19/00* (2011.01)
*A61B 34/10* (2016.01)
(Continued)

(52) U.S. Cl.
CPC ............ *G06T 19/006* (2013.01); *A61B 5/055* (2013.01); *A61B 6/032* (2013.01); *A61B 6/037* (2013.01); *A61B 8/0841* (2013.01); *A61B 34/10* (2016.02); *A61B 34/76* (2016.02); *A61B 90/20* (2016.02); *A61B 90/361* (2016.02); *G06F 19/00* (2013.01); *G06T 7/246* (2017.01); *G06T 7/73* (2017.01); *G16H 40/63* (2018.01); *G16H 50/50* (2018.01); *A61B 2017/00119* (2013.01); *A61B 2034/107* (2016.02); *A61B 2034/2055* (2016.02); *A61B 2034/2063* (2016.02); *A61B 2034/2068* (2016.02); *A61B 2090/364* (2016.02); *A61B 2090/367* (2016.02); *A61B 2090/372* (2016.02); *A61B 2090/3983* (2016.02); *G06T 2207/10016* (2013.01); *G06T 2207/10072* (2013.01); *G06T 2207/30016* (2013.01); *G06T 2207/30096* (2013.01); *G06T 2207/30204* (2013.01); *G06T 2210/41* (2013.01)

(58) Field of Classification Search
CPC ... G06T 19/006; A61B 34/10; A61B 2090/20; A61B 2090/361; A61B 2090/365; A61B 8/0841; A61B 2034/2063
See application file for complete search history.

(56) References Cited

U.S. PATENT DOCUMENTS 9,990,776 B2 * 6/2018 Jagga ..................... G16H 40/63

* cited by examiner

*Primary Examiner* — Ryan R Yang

(57) ABSTRACT

The present disclosure teaches a system and method for communicating the spatial position and orientation of surgical instruments with respect to a surgical area of interest. Using a visual display of a surgical site generated by a camera feed, a computer generates a virtual overlay of the location and projected trajectory of a surgical instrument based on its current position and orientation. Position and orientation information is generated and stored using tracking markers and a tracking sensor in information communication with the computer.

16 Claims, 13 Drawing Sheets

Related U.S. Application Data 2014, now Pat. No. 9,990,776, which is a continuation-in-part of application No. PCT/CA2014/050266, filed on Mar. 14, 2014.

(51) Int. Cl.

| | |
|---|---|
| *A61B 34/00* | (2016.01) |
| *A61B 90/20* | (2016.01) |
| *A61B 90/00* | (2016.01) |
| *G06T 7/73* | (2017.01) |
| *A61B 5/055* | (2006.01) |
| *A61B 6/03* | (2006.01) |
| *A61B 8/08* | (2006.01) |
| *G06T 7/246* | (2017.01) |
| *G16H 40/63* | (2018.01) |
| *G16H 50/50* | (2018.01) |
| *G06F 19/00* | (2018.01) |
| *A61B 34/20* | (2016.01) |
| *A61B 17/00* | (2006.01) |

SYSTEM AND METHOD FOR PROJECTED TOOL TRAJECTORIES FOR SURGICAL NAVIGATION SYSTEMS

CROSS-REFERENCE TO RELATED APPLICATIONS

This application claims priority to International Application No. CA/2014/050266, titled "SYSTEM AND METHOD FOR DYNAMIC VALIDATION, CORRECTION OF REGISTRATION FOR SURGICAL NAVIGATION" and filed on Mar. 14, 2014, the entire contents of which are incorporated herein by reference.

FIELD

The present disclosure relates to an apparatus and method for communicating to a user the relative distance of an object located within a surgical area of interest relative to a surgical instrument operating in said surgical area of interest. The present system may be used with any compatible surgical navigation system. A non-limiting example of such a surgical navigation system is outlined in the PCT International application CA/2014/050270 entitled "SYSTEMS AND METHODS FOR NAVIGATION AND SIMULATION OF INVASIVE THERAPY", which claims the priority benefit of U.S. Provisional Patent Application Ser. Nos. 61/800,155 and 61/924,993, and wherein for the purposes of this present United States Patent Application, the Detailed Description, and Figures of PCT International application CA2014050270 are incorporated herein by reference.

BACKGROUND

In presently performed minimally invasive navigated surgeries surgeons often operate on the patient through a small corridor such as an access port. The corridors normally have very small openings for tools or other medical equipment. This limits their visibility of the surgical operating area due to the small corridors and areas the operations take place in. To enhance visibility of the area they generally use a heads up display or microscope which shows the surgical site of interest at a greater magnification. But this results in issues with tool navigation, specifically depth perception, as with a single camera, depth of tools cannot be gauged by the surgeon.

Thus, there is a need for mechanisms to provide this information to the surgeon in a consistent manner and one in which they can utilize without hindering other aspects of the surgical procedure. The invention disclosed herein attempts to improve the depth perception of the surgeon by providing a mechanism for attaining and communicating such information to the surgeon, thereby attempting to improve presently performed minimally invasive surgeries.

SUMMARY

The present disclosure is generally related to image guided medical procedures using an access port. This port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Disclosed herein is a system and method for communicating a distance of a surgical instrument from an object in a surgical area of interest. An embodiment of a system for communicating a distance of a surgical instrument from an object in a surgical area of interest, comprises:

a surgical instrument;

at least one non-contact distance acquiring device in a known relative position and orientation with respect to the surgical instrument;

a computer processor, in data communication with the at least one non-contact distance acquiring device, the computer processor being programmed with instructions to compute a distance between said surgical instrument and the object in the surgical area of interest; and a communication device for communicating the distance to a user.

A method for communicating a distance of a surgical instrument from an object in a surgical area of interest, comprises:

determining a relative position and orientation between at least one non-contact distance acquiring device and a surgical instrument;

acquiring a first distance, between said at least one non-contact distance acquiring device and the object in the surgical area of interest;

computing, using the determined relative position and orientation and the first distance, a second distance between the surgical instrument and the object; and communicating the second distance to a user.

Additionally, a camera for acquiring an image feed of the surgical area of interest may be included. The camera having a known position and orientation with respect to the surgical instrument, and being in information communication with the computer processor. Said processor being programmed with instructions to overlay onto the image feed, generated on a visual display, a visual cue depicting the distance between said surgical instrument and the object. The overlay may also depict a projected trajectory of the surgical instrument. This projected trajectory may take the form of a line. The visual cue may inform a user of the distance from the surgical instrument to the object by changing the characteristics of the line generated on the visual display at the point where the trajectory would intersect with the object.

A tracking system may be employed to determine the relative positions and orientations of surgical equipment in the operating room such as one or more of the camera, the surgical instrument and the non-contact distance acquiring device. Using one or more tracking marker assemblies attachable to components of the surgical equipment, a tracking sensor may continuously monitor their relative positions and orientations.

The object in the surgical area of interest may include tissue of a patient being operated an implant, or other objects that would potentially be located in the surgical operating area. The distance acquiring device may be a laser range finder, a structured light detection device for 3D imaging, an ultrasonic transducer, or any other non-contact device capable of determining the distance of an object relative to itself.

The camera may be an MRI, a CT scanner, an X-ray scanner, a PET scanner, an ultrasonic scanner or a digital camera. The visual display can be a digital display, a heads-up display, a monitor, a navigation instrument display or a microscope display.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
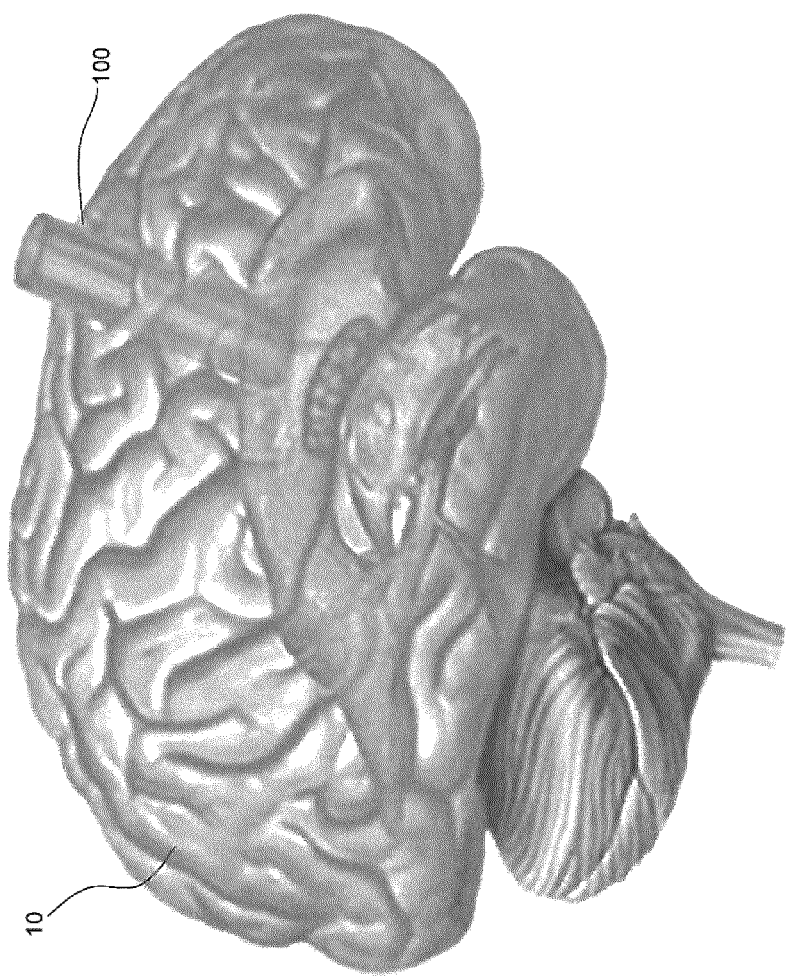
FIG. 1A illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Various apparatuses or processes will be described below to provide examples of embodiments of the invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or processes described below. It is possible that an apparatus or process described below is not an embodiment of any claimed invention.

Furthermore, numerous specific details are set forth in order to provide a thorough understanding of the embodiments described herein. However, it will be understood by those of ordinary skill in the art that the embodiments described herein may be practiced without these specific details. In other instances, well known methods, procedures and components have not been described in detail so as not to obscure the embodiments described herein. Also, the description is not to be considered as limiting the scope of the embodiments described herein.

Furthermore, in the following passages, different aspects of the embodiments are defined in more detail. In particular, any feature indicated as being preferred or advantageous may be combined with at least one other feature or features indicated as being preferred or advantageous.

Embodiments of the present disclosure provide overlays of medical equipment for assisting a surgeon in visualizing a surgical area or object of interest such as a medical instrument, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

An example of an access port is an intracranial conduit which may be employed in neurological procedures in order to provide access to internal tissue pathologies, such as tumors. One example of an intracranial access port is the BrainPath™ surgical access port provided by NICO, which may be inserted into the brain via an obturator with an atraumatic tip. Such an access port may be employed during a surgical procedure, by inserting the access port, via the obturator that is received within the access port, through the white and gray of the brain to access a surgical site.

Minimally invasive brain surgery using access ports is a recently conceived method of performing surgery on brain tumors previously considered inoperable. One object of the present invention is to provide a system and method to assist in minimally invasive brain surgery. To address intracranial surgical concerns, specific products such as the NICO Brain-Path™ port have been developed for port-based surgery.

FIG. 1A illustrates the insertion of an access port 100 into a human brain 10, for providing access to internal brain tissue during a medical procedure. In FIG. 1A, access port 100 is inserted into a human brain 10, providing access to internal brain tissue. Surgical instruments (which includes any surgical equipment a surgeon may insert into brain tissue including surgical tools such as scalpels, needles, biopsy probes, suctioning devices, scissors to mention just a few) may then be inserted within the lumen of the access port 100 in order to perform surgical, diagnostic and/or therapeutic procedures, such as resecting tumors as necessary.

As seen in FIG. 1A, port 100 is comprised of a cylindrical assembly formed of an outer sheath. Port 100 may accommodate an introducer (not shown) which is an internal cylinder that slidably engages the internal surface of port 100. The introducer may have a distal end in the form of a conical atraumatic tip to allow for insertion into the sulcal folds of the brain 10. Port 100 has a sufficient diameter to enable bimanual manipulation of the surgical instrument(s) within its annular volume such as suctioning devices, scissors, scalpels, and cutting devices as examples.

Figure 1B:
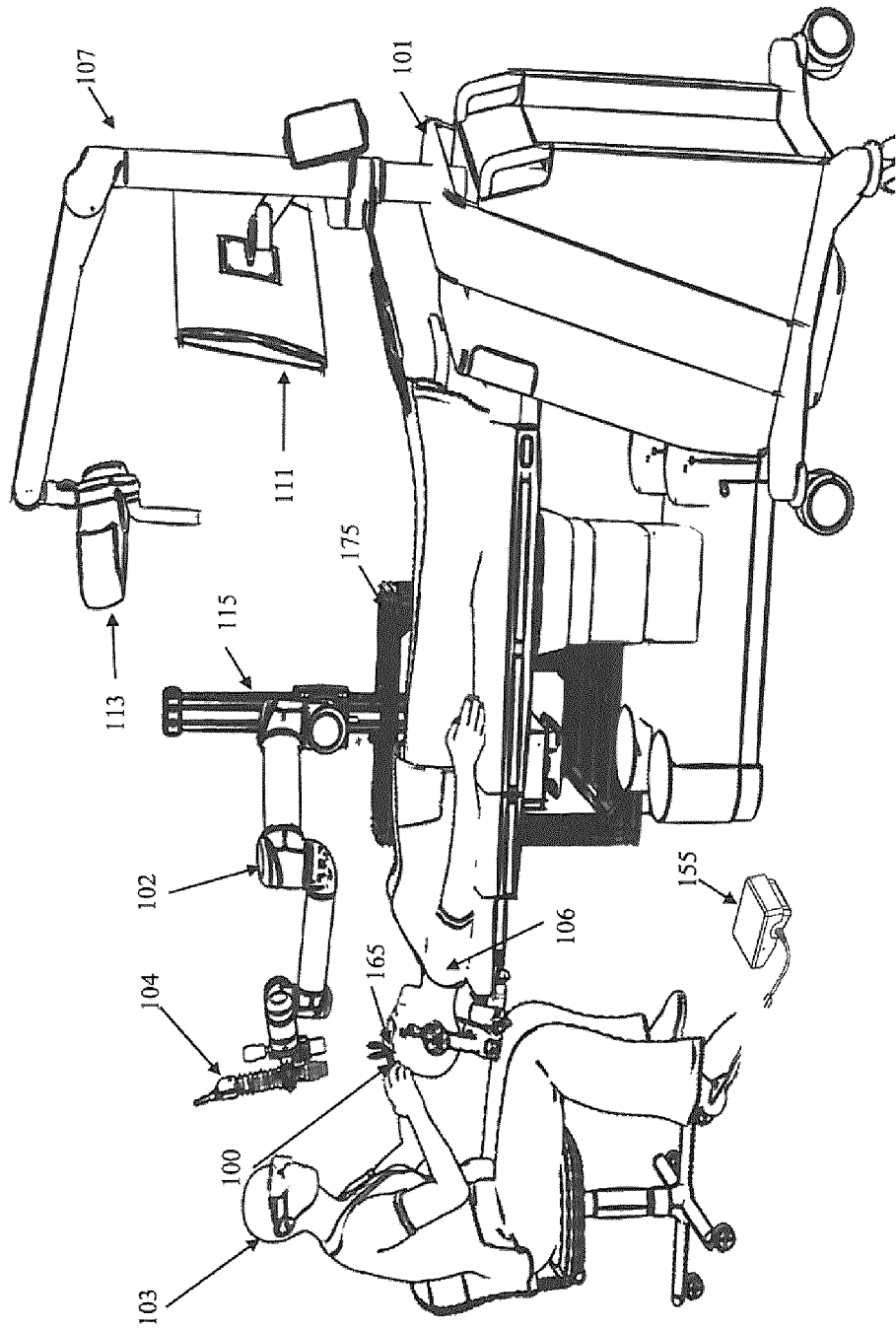
FIG. 1B is a diagram illustrating components of an exemplary surgical system used in port based surgery.

FIG. 1B is a diagram illustrating components of an exemplary surgical system used in port based surgery. FIG. 1B shows a navigation system 107 having an equipment tower 101, tracking system 113, display 111 (for a graphical user interface), an intelligent positioning system 175 and tracking markers 165 used to track surgical instruments or access port 100. Tracking system 113 may also be considered an optical tracking device which tracks the tracking markers 165. The tracking system may include a tracking camera.

As shown in FIG. 1B, surgeon 103 is resecting a tumor in the brain of a patient 106, through port 100. External scope 104, attached to automated arm 102, is typically used by the surgeon to enhance visibility of the brain at the distal end of the port 100. The external scope 104 may be zoomed-in or zoomed-out, and its output depicted on a visual display 111 which may be overlaid with a virtual imaging feed of virtual medical instruments contained in the field of view of the external scope 104. The overlays may include the medical instruments projected trajectories, as will be discussed in more detail below, allowing for the visualization of the instruments trajectories and their respective distances from imminent structures.

Figure 2:
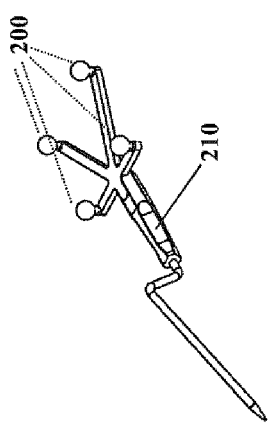
FIG. 2 illustrates a surgical instrument with attached tracking markers.

In an embodiment, an overlay of a surgical instrument visualization and patient imaging information on a video image feed of the surgical field is provided during a procedure. An example surgical instrument is shown at 210 in FIG. 2, which includes a pointer segment 212 and landmarks 200 (four (4) shown) which is used to verify registration and locate preoperatively determined anatomical structures during navigated surgical procedures.

Figure 3:
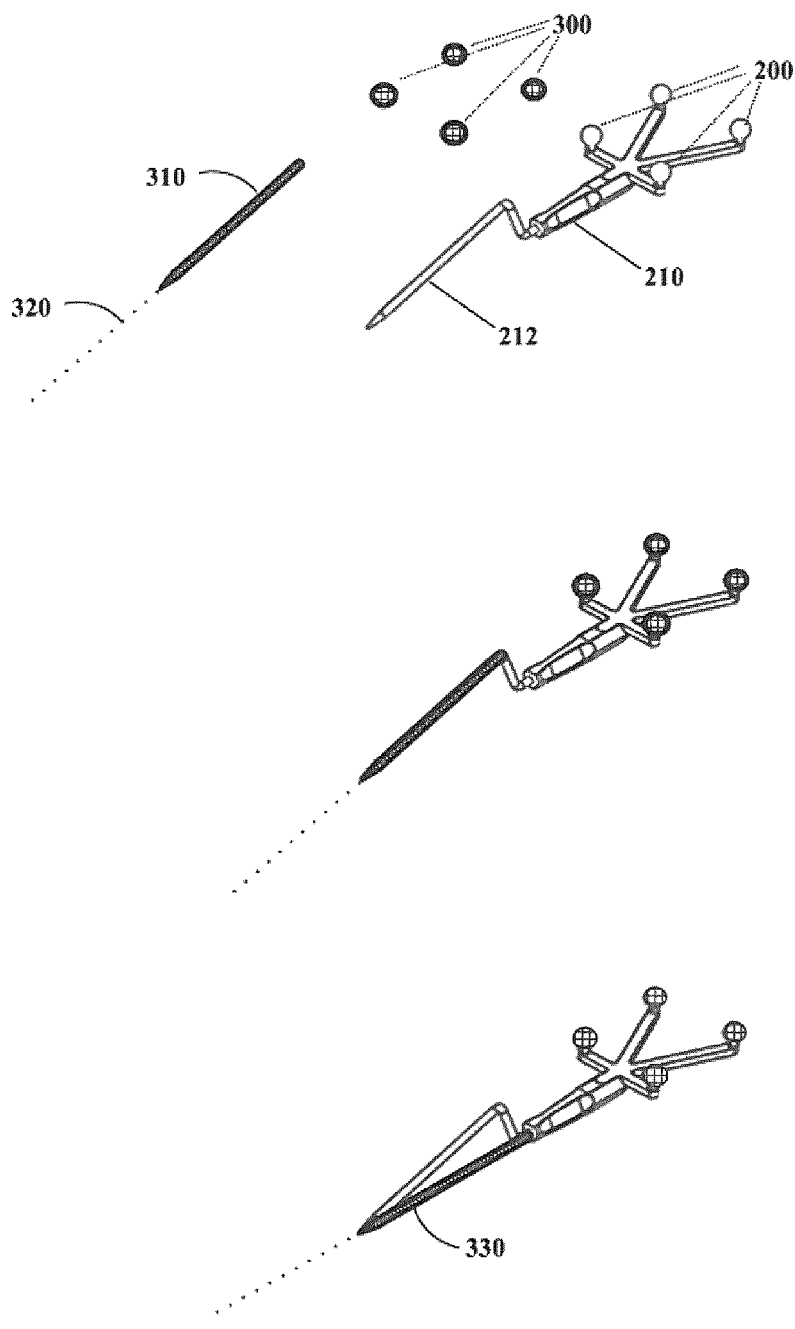
FIG. 3 illustrates a surgical instrument with attached tracking markers and the alignment of its corresponding virtual overlay.

In FIG. 3 an actual surgical tool 210 with its associated landmarks 200 and its associated virtual object representation comprised of virtual landmarks 300, virtual pointer segment 310, and projected extension of a virtual pointer segment 320 are shown. In this exemplary illustration, the virtual representation of the pointer tool 210 has a projected extension 320 out of the distal end of the tool positioned along the tools central axis shown as a dotted line. This extension depicts the trajectory of the tools distal tip given its path is coaxial with the pointer segment 310 of the tool. The projected extension 320 in addition to providing trajectory information also provides a visual cue as to the distance of the end of the tool 210 from an imminent structure (either tissue or any other form of detectable matter). The visual cue may be provided by changing the colour, thickness, pattern or any other characteristic of the projected extension to portray the point at which the projected extension penetrates an imminent structure.

The surgical instrument 210 may be tracked with one or more sensors which are in communication with one or more transceiver(s) of the tracking system that receives, records and/or processes the information regarding the instrument(s) that the sensor(s) are detecting. The sensors may track, among other things, the spatial position of the instrument(s), including its angle and orientation (i.e. pose). Information regarding the distance of the distal end of the tool 210 from an imminent structure may be determined using a structured light scan of the region in which the distal end of the instrument is located, a laser range detector located on the tool 210, or another applicable mechanism not described here.

Persons skilled in the art will appreciate that being able to visualize a medical instrument, its trajectory path, and distance from imminent structures when it is within the vicinity of a patient will aid in the improvement of the accuracy of, and time required for, the procedure.

Active or passive fiduciary markers may be placed on the port 100 and/or imaging sensor 104, and/or any medical instruments 210 to determine the location of these objects using the tracking camera 113 and navigation system.

These markers (such as 200 shown in FIG. 2) may be reflective spheres configured to be seen by the stereo camera of the tracking system to provide identifiable points for tracking. A tracked instrument tracked by the tracking system 113 is typically defined by a grouping of markers such as markers 200 of instrument 210, which identify a volume and any projected extensions thereof, and are used to determine the spatial position and pose of the volume of the tracked instrument in three dimensions. Typically, in known exemplary tracking systems a minimum of three spheres are required on a tracked tool to define the instrument's spatial position and orientation; however it is known in the art that the use of four markers is preferred. For example tool 210 shown in FIG. 2 uses four (4) optical tracking markers 200.

Markers may be arranged statically on a target on the outside of the patient's body or connected thereto. Tracking data of the markers acquired by the stereo camera are then logged and tracked by the tracking system. An advantageous feature is the selection of markers that can be segmented easily by the tracking system against background signals. For example, infrared (IR)-reflecting markers and an IR light source from the direction of the stereo camera can be used. Such a tracking system is known, for example, the "Polaris" system available from Northern Digital Inc.

In an embodiment, the navigation system may utilize reflective spherical markers in combination with a stereo camera system, to determine spatial positioning and pose of the medical instruments and other objects within the operating theater. Differentiation of the types of medical instruments and other objects and their corresponding virtual geometric volumes and projected extensions could be determined by the specific orientation of the reflective spheres relative to one another giving each virtual object an individual identity within the navigation system. This allows the navigation system to identify the medical instrument or other object and its corresponding virtual overlay representation (i.e. the correct overlay volume) as seen as 310 in FIG. 3. The location of the markers also provide other useful information to the tracking system, such as the medical instrument's central point, the medical instrument's central axis and orientation, and other information related to the medical instrument. In an embodiment the mentioned useful information may be utilized to define the projected extension of the volume representing its trajectory such as 320 in FIG. 3. This trajectory may be defined arbitrarily given it has medical utility, such as the trajectory of a suturing needle when used to pierce tissue. The virtual overlay representation of the medical instrument may also be determinable from a database of medical instruments.

As mentioned above in an embodiment the distance of the distal end of probe of the medical instrument 210 from an imminent structure may be determined using a laser range finder or a structured light scan. These implementations will be described below in more detail.

Alternative markers may include radio frequency (RF), electromagnetic (EM), pulsed and un-pulsed light emitting diodes (LEDs), glass spheres, reflective stickers, unique structures and patterns. Further, the RF and EM markers may have specific signatures for the specific tools they would be attached to. The reflective stickers, structures and patterns, glass spheres, LEDs could all be detected using optical detectors, while RF and EM could be picked up using antennas. Advantages to using EM and RF tags would include removal of the line-of-sight condition during the operation, whereas using an optical-based tracking system removes the additional noise and distortion from environmental influences inherent to electrical emission and detection systems.

In a further embodiment, 3-D design markers could be used for detection by an auxiliary camera and/or optical imaging system. Such markers could also be used as a calibration pattern to provide distance information (3D) to the optical detector. These identification markers may include designs such as concentric circles with different ring spacing, and/or different types of bar codes. Furthermore, in addition to using markers, the contours of known objects (i.e., side of the port) could be made recognizable by the optical imaging devices through the tracking system.

For accurate overlays to be produced the first step is to define a common coordinate space composed of both an actual coordinate space and a virtual coordinate space. Where the actual coordinate space contains actual objects that exist in space, virtual coordinate space contains virtual objects that are generated in a virtual space, and the common coordinate space contains both the aforementioned actual and virtual objects.

It should be noted that the virtual objects may also be comprised of landmarks that can be used to associate them (i.e. their spatial positions and poses) with their respective actual objects. These landmarks are placed in predetermined virtual positions relative to the virtual objects and are correlated with actual landmarks placed in predetermined positions relative to the respectively associated actual objects. Examples of such landmarks are provided in FIG. 3. In the figure virtual landmarks 300 are located in a predetermined position relative to the virtual object comprising of the pointer segment 310 and pointer extension 320. Actual landmarks 200 are also located in a predetermined position relative to the actual objects they're connected to. It should be noted that the virtual and actual objects spatial relationships (i.e. spatial position and pose) relative to their respective virtual and actual landmarks are predefined within the system. It should also be noted that the generation of the virtual object (including its landmarks) in a specified position and pose (spatial relationship) relative to the actual landmarks in the common coordinate frame is also predefined within the system. These relationships are then used to generate the virtual objects with a specific position and pose relative to the actual objects position and pose in the common coordinate frame.

An example of such relationships is shown in FIG. 3. In the figure it can be seen that the virtual landmarks, when aligned with the actual landmarks create an accurate overlay of the virtual object on the actual object. In some embodiments the virtual objects may mirror the actual objects in characteristics such as but not limited to size, shape, texture, colour, location, and etc. For example virtual pointer segment 310 mimics the shape and location of the actual objects pointer segment as depicted in FIG. 3. While in alternate embodiments the virtual object representation can be an arbitrary size, shape, texture, colour, location, and etc. that provides a useful information to the user. For example virtual pointer segment 330 mimics the direction of the pointer handle and provides information about the location of the tip of the actual pointer, but does not mimic the actual object with respect to its shape.

Figure 4:
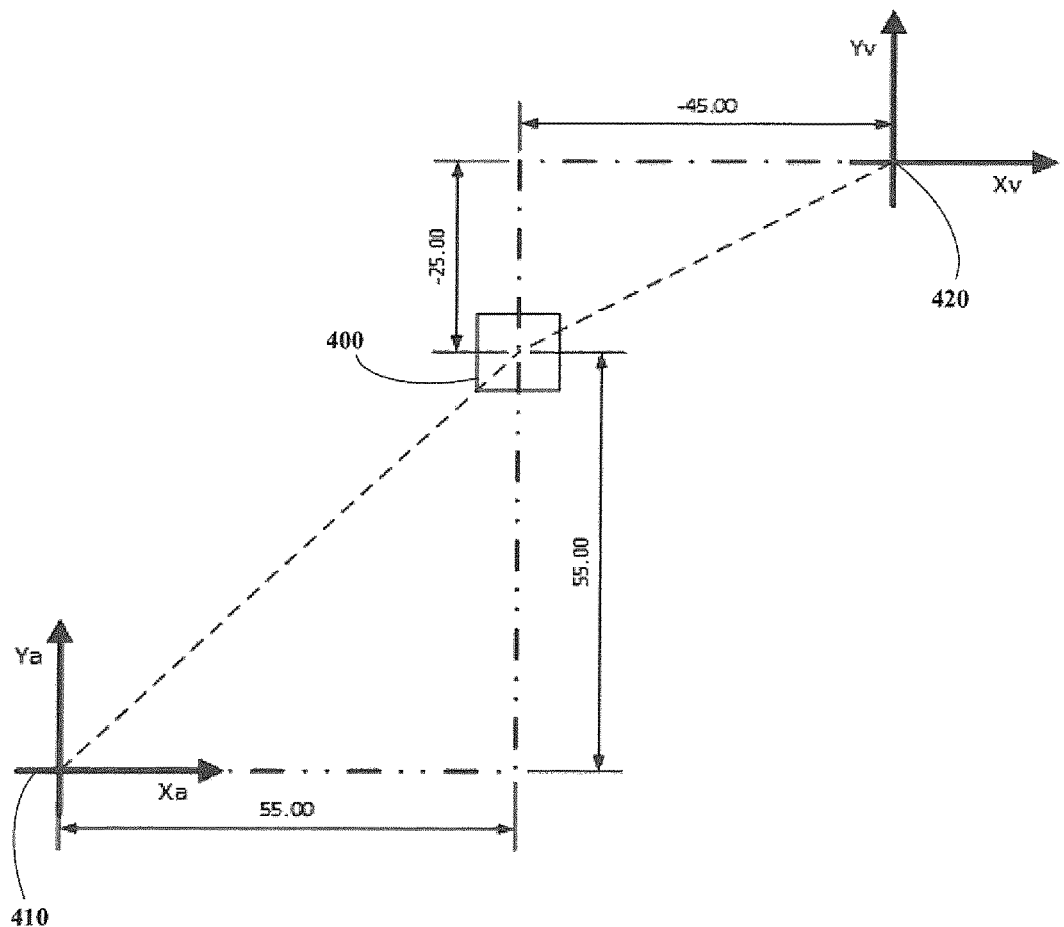
FIG. 4 illustrates a diagram depicting the union of two coordinate spaces.

In order to form a common coordinate space composed of the amalgamated virtual and actual coordinate spaces, the two spaces must be coupled with a common reference coordinate, having a defined position and pose that can be located in both the actual and virtual coordinate spaces. An example of such a reference coordinate 400 and actual and virtual coordinate space origins, 410 and 420, are provided in FIG. 4. Once the common reference coordinate location (i.e. position and pose) is acquired in both spaces they can be used to correlate the position and pose (coordinates) of any point in one coordinate space to the other. The correlation is determined by equating the locations of the common reference coordinate in both spaces and solving for an unknown translation variable for each degree of freedom defined in the two coordinate spaces. These translation variables may then be used to transform a coordinate in one space to an equivalent coordinate in the other. An example correlation can be derived from the diagram in FIG. 4 depicting a two dimensional coordinate space. In the figure the common reference coordinates 400 position are determined relative to the actual coordinate space origin 410 and the virtual coordinate space origin 420. These common reference coordinates can be derived from the diagram as:

$$(X_{cra}, Y_{cra}) = (55, 55) \text{ and}$$

$$(X_{crv}, Y_{crv}) = (-25, -45)$$

Where the subscript "cra" denotes the common reference coordinate position relative to the actual coordinate space origin and the subscript "crv" denotes the common reference coordinate position relative to the virtual coordinate space origin. Utilizing a generic translation equation describing any points (($Y_a$, $X_a$) and ($Y_v$, $X_v$)), where the subscript "a" denotes the coordinates of a point relative to the actual coordinate space origin 410, and the subscript "v" denotes the coordinate of a point relative to the virtual coordinate space origin 420, we can equate the individual coordinates from each space to solve for translation variables (($Y_T$, $X_T$)), where the subscript "T" denotes the translation variable as shown below.

$$Y_a = Y_v + Y_T$$

$$X_a = X_v + X_T$$

Now substituting the derived values of our points from FIG. 4 we can solve for the translation variable.

$$55 = -45 + Y_T$$

$$100 = Y_T$$

and $$55 = -25 + X_T$$

$$80 = X_T$$

Utilizing this translation variable, any point ((i.e. ($Y_v$, $X_v$)) in the virtual coordinate space may be transformed into an equivalent point in the actual coordinate space through the two generic transformation equations provided below. It should be noted that these equations can be rearranged to transform any point from the actual coordinate space into an equivalent point in the virtual coordinate space as well.

$$Y_a = Y_v + 100$$

and $$X_a = X_v + 80$$

This will allow the virtual and actual objects respective equivalent positions and poses to therefore be defined in both the actual and virtual common coordinate spaces simultaneously. Once the correlation is determined the actual and virtual coordinate spaces become coupled and the resulting common coordinate space can be used to overlay virtual and real objects when imaged. It should be noted that these virtual and real objects can be superimposed in the common coordinate space.

Furthermore, the above-mentioned computation can also be used in computer readable instructions to track the position and orientation (or equivalently pose) of the surgical instrument, the non-contact distance acquiring device and the position of a proximal surface of an object. Once initial coordinates are generated and stored in the computer by calibrating the spatial relationship between the non-contact distance acquiring device and the surgical instrument, using combined readings from the non-contact distance acquiring device, providing the distance between the device and the proximal surface of the object, and the readings from the tracking markers, providing the relative motion between the non-contact distance acquiring device and the surgical instrument, a computer can track the relative locations of the surgical instrument, the non-contact distance acquiring device and object.

Figure 5:
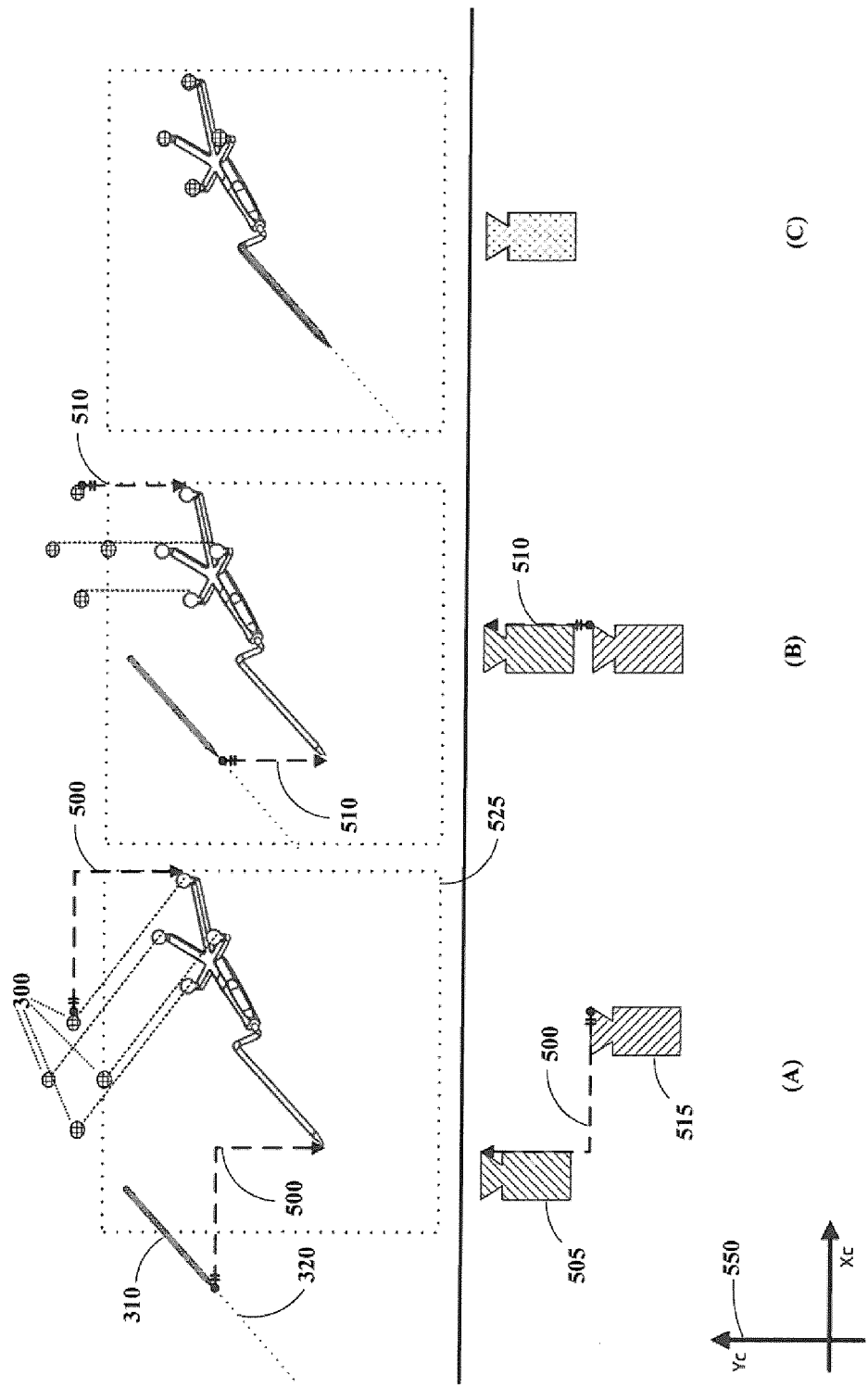
FIG. 5 illustrates a diagram depicting the alignment of a virtual and actual imaging feed.

The second step in producing an accurate overlay is to identify an actual camera(s) of which the imaging feed is to be overlaid with a virtual imaging feed from a virtual camera, where both cameras are located within the common coordinate space. Examples of such cameras are shown in FIG. 5. In the figure a diagram is shown comparing the position and pose of the virtual and actual cameras, 505 and 515, in the common coordinate space and their respective imaging feeds. Once the actual camera is identified its position and pose in the common coordinate space 550 must be acquired. When this is complete the virtual camera must be constrained to have the equivalent spatial position and pose as the actual camera. This can be accomplished by applying the transform described in detail above. In addition this virtual camera should have the same optical properties as the actual camera, namely, the same field-of-view, aspect ratio, and optical distance in order to provide the same perspective view of the common coordinate space as the actual camera (given the virtual and actual objects have the same location in the common coordinate space) as depicted in FIG. 5 (C).

The third step in producing an accurate overlay is to project the imaging feed from both the actual and virtual cameras onto a display (allowing for some or no transparency effect in one of the feeds). This will produce an overlay of the virtual objects on their associated actual object counterparts. The actual camera will capture the view of the actual objects in the common coordinate space while the virtual camera will capture a view of the virtual objects in the common coordinate space. FIG. 5 depicts a situation in which the virtual camera 505 is not aligned with an actual camera 515 in the common coordinate frame 550 to illustrate the need for a correct alignment of the virtual 505 and actual 515 cameras to produce an accurate overlay. In the figure the display 525 containing imaging feeds from both the actual and virtual cameras in the common coordinate frame is shown. The arrows 500 and 510 represent the discrepancy in alignment of the cameras and consequently the overlay on the display. As the virtual camera is moved left from FIG. 5A to FIG. 5B it can be seen that the overlay consisting of 310, 320, and 300 progressively moves right, closer to a correct alignment. As the diagram moves from FIG. 5B through to FIG. 5C along the discrepancy path shown by arrow 510, the cameras become coincident and the overlay moves in the opposite direction in the display to become correctly aligned as can be seen in FIG. 5C. The explanation of FIGS. 5A to 5C above is to illustrate the effect of incorrect alignment of the cameras and to provide reasoning as to why correct alignment is a necessity when producing accurate overlays. In common practice the virtual camera and virtual objects will be constantly generated coincidently at the location (position and pose) of the actual camera and corresponding actual objects. In general both cameras will have the same perspective view of the common coordinate space including any actual and virtual objects contained within, because of the cameras identical optical properties and positions and poses. Therefore any virtual objects should substantially align with their associated actual object counterparts, if they are generated in the equivalent position and pose as them in the common coordinate frame. If this overlay is executed periodically this can allow for a real-time overlaid imaging feed of the surgical site of interest.

The system and method disclosed herein is implemented using at least one non-contact distance acquiring device in a known relative position and orientation with respect to the surgical instrument. The non-contact distance acquiring device may be attached to the surgical instrument or may be at a remote location from the surgical instrument. The system includes a computer processor, in data communication with the one or more non-contact distance acquiring devices. The computer processor is programmed with instructions to compute a distance between the surgical instrument and the object in the surgical area of interest. A communication device for communicating the distance to a user is connected to the computer processor.

Additionally, a camera for acquiring an image feed of the surgical area of interest may be included. The camera has a known position and orientation with respect to the surgical instrument, and being in information communication with the computer processor, is programmed with instructions to overlay onto the image feed, generated on a visual display, a visual cue depicting the distance between the surgical instrument and the object. The overlay may also depict a projected trajectory of the surgical instrument. This projected trajectory may take the form of a line with specific characteristics. The visual cue may inform a user of the distance to an object by changing the characteristics of the line generated on the visual display at the point where the trajectory would intersect with the object. Some non-limiting examples of line characteristics that can be changed include color, thickness, line pattern and any combination thereof.

A tracking system can be employed to determine the relative positions and orientations of surgical equipment located in the operating area consisting of one or any combination of the camera, the surgical instrument and the distance acquiring device. Using one or more tracking markers attachable to the components of the mentioned surgical equipment, a tracking sensor can continuously monitor relative positions and orientations of the surgical equipment.

The object in the surgical area of interest can include tissue of a patient being operated on, an implant, or any other objects located in the surgical area of interest. The distance acquiring device can be a laser range finder, a structured light detection device for 3D imaging, an ultrasonic transducer, or any other non-contact device capable of determining the distance of an object relative to itself.

The detector may include an MRI, a CT scanner, an X-ray scanner, a PET scanner, an ultrasonic scanner or a digital camera. Non-limiting examples of the visual display may be a digital display, a heads-up display, a monitor, a navigation instrument display or a microscope display.

Distance thresholds can be stored in the computer such that when the distance between the surgical instrument and the object reduces below or reaches the threshold distance the computer processor is programmed with instruction to signal an alert. The alert can be a visual alert generated on the visual display or elsewhere, an audio alert or a tactile alert such as activating a vibrating member.

An exemplary embodiment of the system disclosed herein is implemented using a laser range finder as shown in FIG. 6. The laser range finder 600 may be mounted to the distal end of a tool 210 for example as depicted in FIG. 6A. As the tool 210 is moved along the path 620 the laser range finder 600 functions by emitting a laser pulse 610 and awaiting the return of the reflected laser pulse 625 reflected off of the object 630 in the direction of the initial pulse 610 as depicted in FIG. 6B. Once the return pulse 625 is detected the laser range finder 600 then calculates the distance to the object 630 that reflected the laser pulse 625. The distance may then be used to alter an overlay, in particular the projected extension 320 at the distance where an imminent object is located providing the surgeon with a visual cue. This can be seen in FIG. 6C where the virtual imaging feed from a virtual camera 515 is shown on the display 525 independent of the actual camera imaging feed for the shown perspective in this view. It should be noted that in this view of the common coordinate space only virtual objects are visible in the absence of the actual camera imaging feed. In FIG. 6C the virtual object representation of the tool 310, in particular its projected extension 320 converts from a dotted extension (indicative of no object) to a dashed extension 660 (indicative of an imminent object) at the point 670 where the imminent object 630 is detected by the laser range finder 600.

Figure 6A:
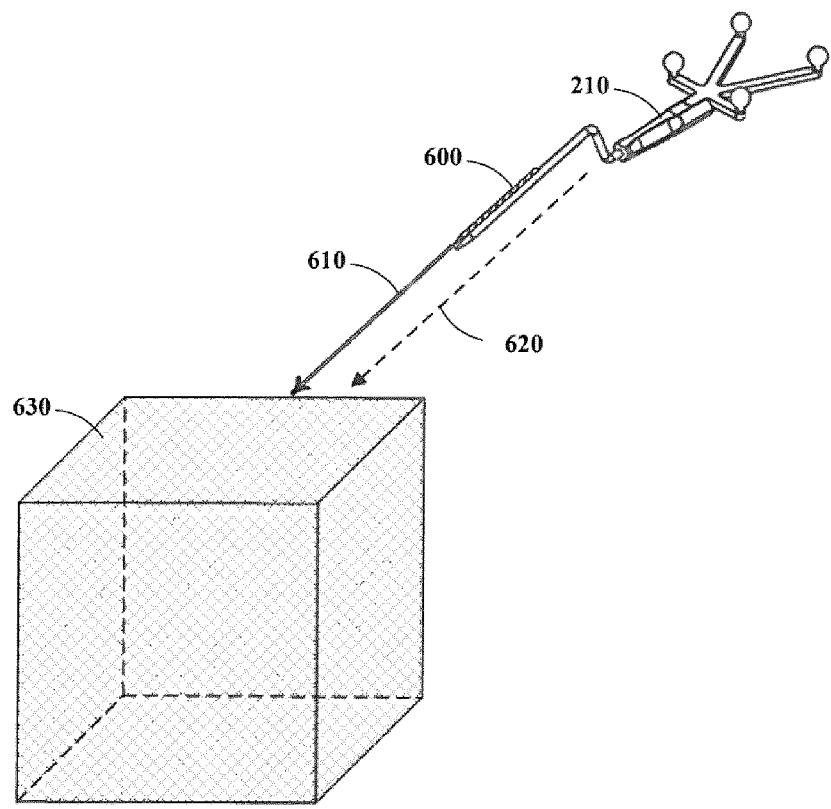
FIG. 6A illustrates a medical instrument with attached laser range finder and its movement trajectory.
Figure 6B:
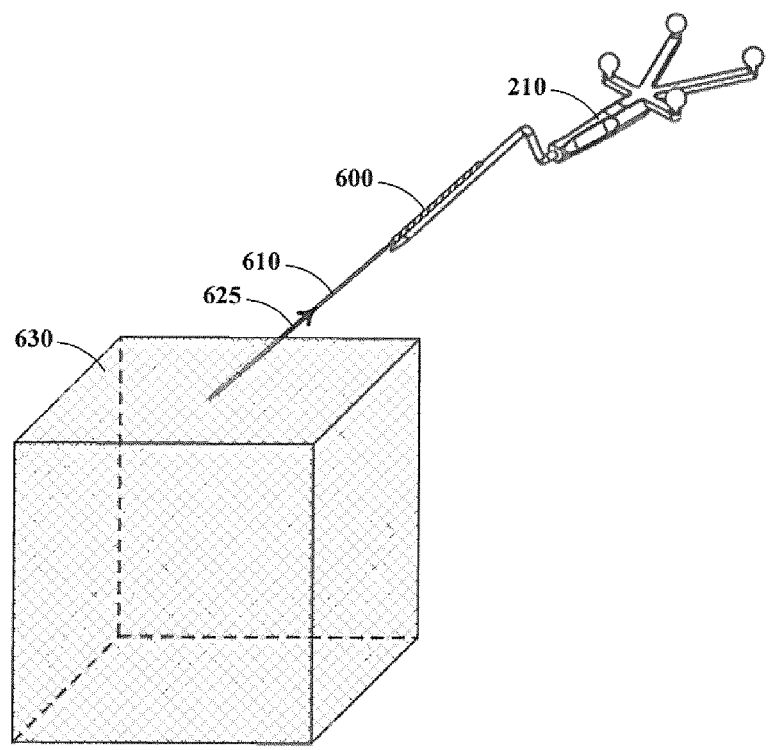
FIG. 6B illustrates a medical instrument with attached laser range finder detecting an imminent object.
Figure 6C:
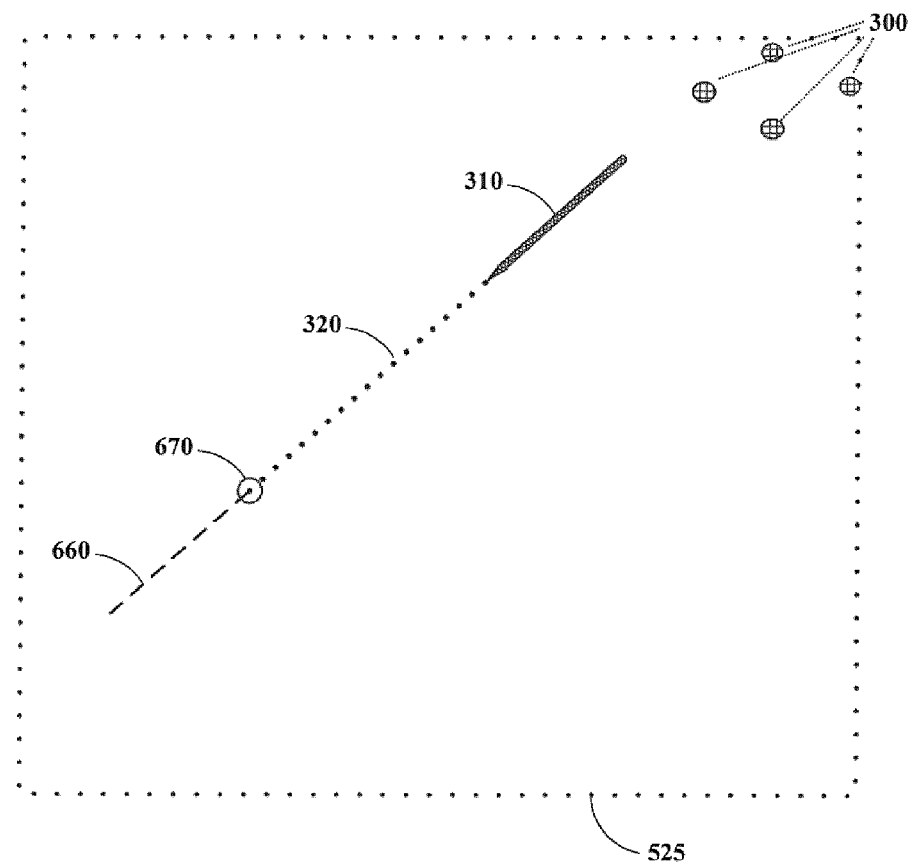
FIG. 6C illustrates a medical instrument with attached laser range finder overlay and its projected trajectory.
Figure 6D:
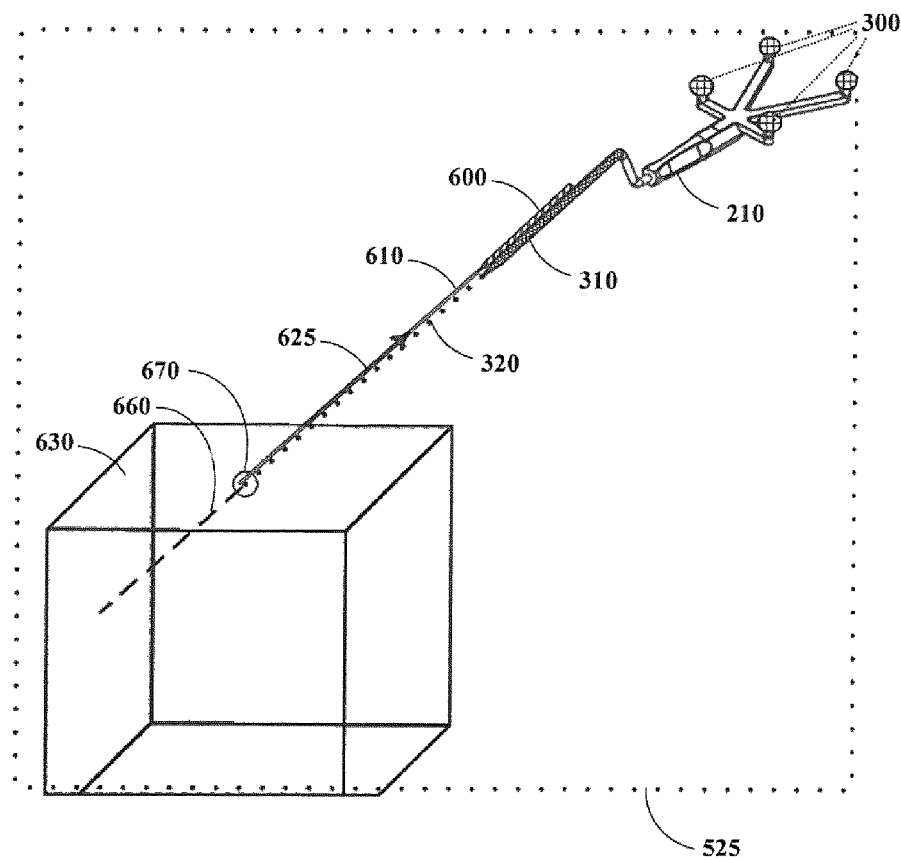
FIG. 6D illustrates a medical instrument with attached laser range finder detecting an imminent object and its corresponding overlay showing its projected trajectory.

The full effect of the virtual projected extension can be seen in FIG. 6D, where the imaging feed from the actual camera 505 and the virtual camera 515 (FIG. 5) are overlaid on the display 525. In the figure the display 525 (FIG. 6D) contains both the real and virtual imaging feeds, and it can be seen that the projected extension 320 can aid a user in determining the distance of an object 630 from the distal end of a surgical tool 210. This is valuable information during navigated surgery as when the surgeon is using a two dimensional display such as the display 525 shown in FIG. 6D there is no depth information available on it and the surgeon's own depth perception is rendered inutile. Therefore indicating the depth of an imminent object in the direction of a tools trajectory to a surgeon, especially when working in a small corridor type setup for a surgery such as the port based surgery mentioned above, allows the surgeon to perform the procedure with greater accuracy and potentially in less time.

Figure 7A:
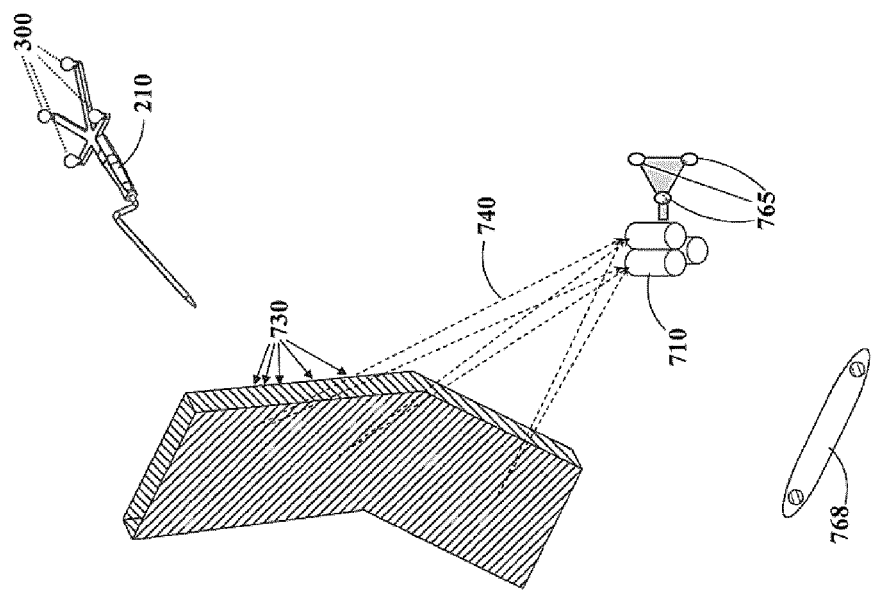
FIG. 7A illustrates a diagram of a medical instrument with an imminent object and detection of the object using structured light.
Figure 7A:
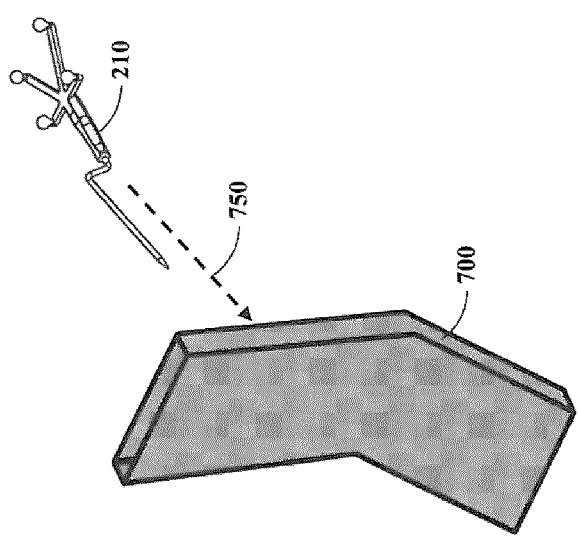

In an alternate embodiment the distance of the distal end of the tool from an imminent structure, in the context of an overlaid image of the surgical field of interest, may be determined using structured light based surface scanning. Referring to FIG. 7A it can be seen that in the left frame there is an imminent object 700 in the trajectory 750 of the surgical instrument. The right frame contains a structured light surface rendering device 710 consisting of two light sensors and a projector. The exemplary structured light device 710 functions by projecting a known structured light pattern 730 onto an object to be rendered, imaging the resultant structured light pattern on the object 740, and then comparing the known structured light pattern with the imaged one to infer the 3D surface of the object.

Once the 3D structure has been inferred it can be transferred into the common coordinate frame as a virtual object in order to interact with other virtual objects, such as the virtual object representation of the tool 210 consisting of landmarks 300, pointer segment 310, and projected extension 320. This can be achieved through the use of a tracking device as described above, an example of which is shown as 768 in FIG. 7A. Using the tracking device the location (spatial position and pose) of the structured light surface rendering device 710 can be determined in the common coordinate frame if the structured light surface rendering device has tracking markers, such as tracking markers 765 shown in FIG. 7A.

Figure 7B:
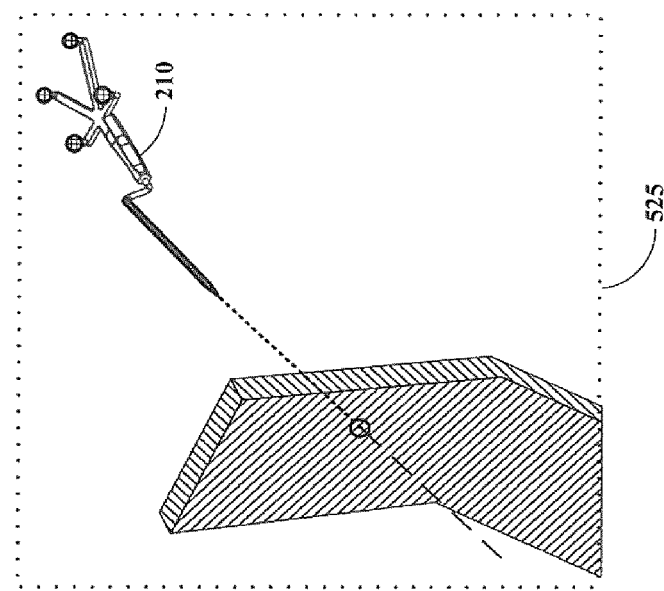
FIG. 7B illustrates a diagram of an overlay of a medical instrument with its projected trajectory on a camera imaging feed.
Figure 7B:
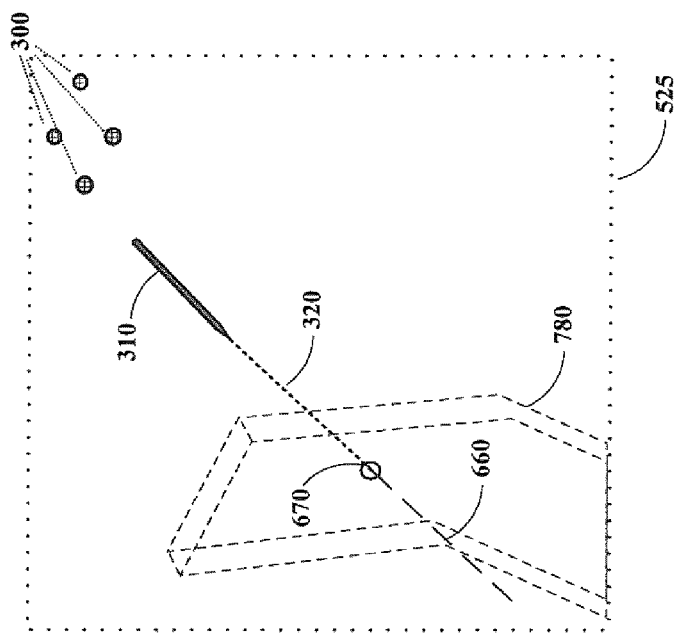

Once the location of the of the surface rendering device 710 is known in the common coordinate space, the 3D surface of the object 700 that was detected by the device 710 can be rendered as a virtual surface in the common coordinate space (because its location becomes known relative to the structured light device) as shown in the left frame of FIG. 7B. The right frame in FIG. 7B depicts the imaging feed of a virtual camera 515 in the display 525. The scene being captured by the imaging feed depicts the interaction of all of the generated virtual objects in the common coordinate frame captured by the virtual camera 515.

Given the virtual object representation 780 of the actual object 700 is now represented in the common coordinate frame. The projected extension 320 in this frame can be configured to change from a dotted extension 320 (indicative of no object) into a dashed extension 660 (indicative of an imminent object) at the point whenever the virtual projected extension comes into contact with the virtual object representation 780, such as the point 670 shown in FIG. 7B. The full effect of the virtual projected extension can be seen in the right frame of FIG. 7B, where the imaging feed from the actual camera 505 and the virtual camera 515 are overlaid on the display 525. In the figure the display 525 contains both the real and virtual imaging feeds, and it can be seen that the projected extension 320 can aid a user in determining the distance of an object 700 from the distal end of a surgical tool 210. This is valuable information during navigated surgery as when the surgeon is using a two dimensional display, such as the display 525 shown in FIG. 7, there is no depth information available on it and the use of a screen renders the surgeon's own depth perception inutile. Therefore indicating the depth of an imminent object in the direction of a tool's trajectory to a surgeon, especially when working in a small corridor type setup for a surgery such as the port based surgery mentioned above, allows the surgeon to perform the procedure with greater accuracy. An example of a mock brain surgery procedure is depicted in FIG. 8 where the projected trajectory of the tool can be seen to change a characteristic as it penetrates the brain volume.

Figure 8:
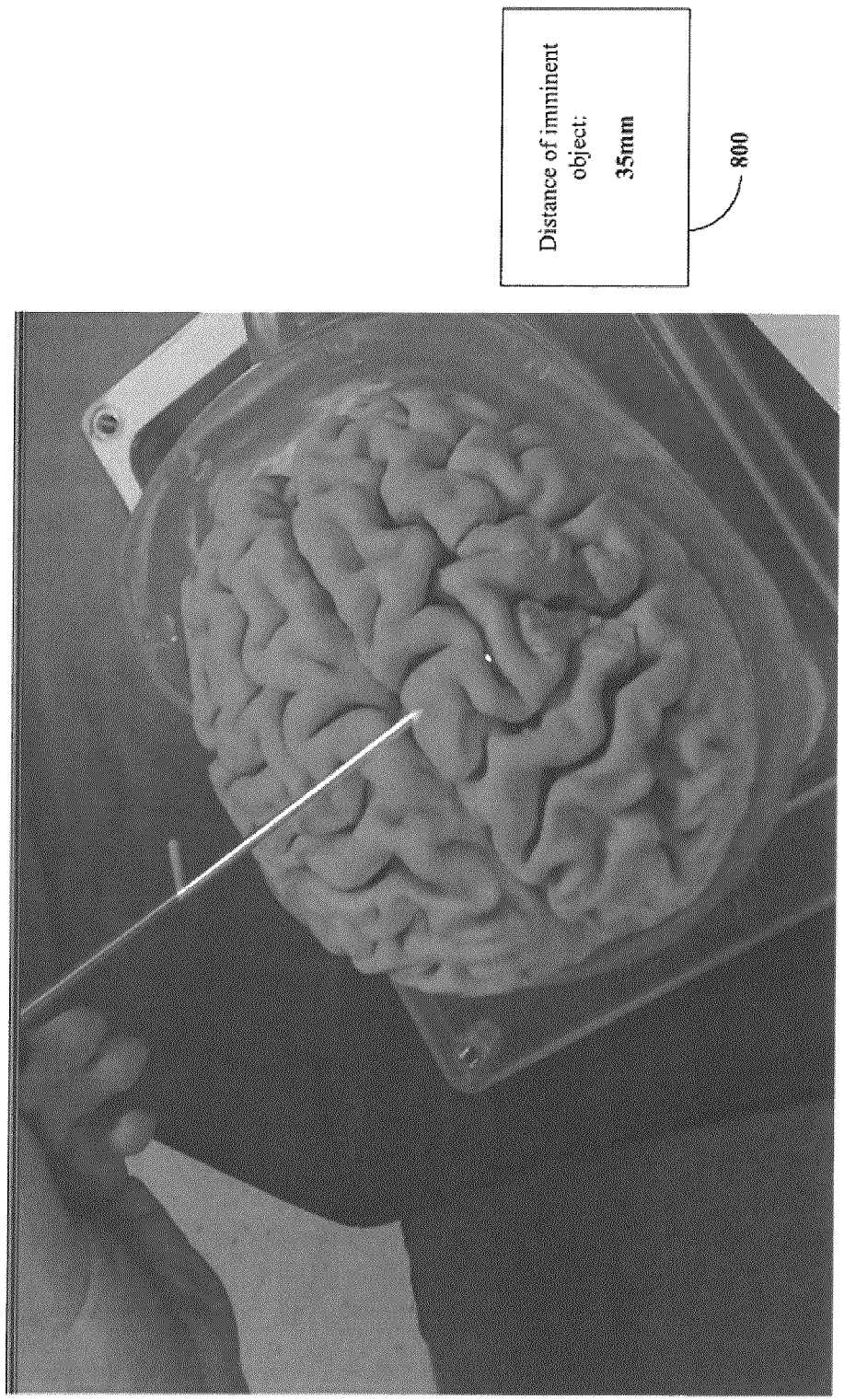
FIG. 8 illustrates an exemplary embodiment of a projected overlay used during a mock surgical procedure relative to a mock brain.

In addition to the mentioned embodiments it may also serve as useful to indicate on the display the distance of the projected trajectory before it contacts an imminent structure as shown as 800 in FIG. 8.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method for communicating a distance of a surgical instrument from an object in a surgical area of interest, comprising:
   determining a relative position and orientation between at least one non-contact distance acquiring device, having a known relative position and orientation, and a the surgical instrument, thereby providing a determined relative position and orientation between the at least one non-contact distance acquiring device and the surgical instrument;
   acquiring a first distance, between said at least one non-contact distance acquiring device, having the known relative position and orientation, and the object in the surgical area of interest;
   computing, using the determined relative position and orientation between the at least one non-contact distance acquiring device and the surgical instrument and the first distance, a second distance between the surgical instrument and the object;
   communicating the second distance; and
   overlaying onto the image feed a projected trajectory of the surgical instrument on a visual display.

2. The method according to claim 1, wherein a visual cue is provided by changing one or more line characteristics of the projected trajectory.

3. The method according to claim 2, wherein said one or more line characteristics include a color, thickness, line pattern, and any combination thereof.

4. The method according to claim 1, wherein the known relative position and orientation of one or more non-contact acquiring devices an imaging detector with respect to the surgical instrument is acquired by a tracking system.

5. The method according to claim 4, wherein said tracking system includes one or more tracking markers on at least the surgical instrument and a tracking sensor for tracking said one or more tracking markers.

6. The method according to claim 1, wherein the object in a surgical area of interest is tissue of a patient being operated on.

7. The method according to claim 1, wherein the non-contact distance acquiring device is a laser range finder.

8. The method according to claim 1, wherein the non-contact distance acquiring device is a structured light detection device for 3D imaging.

9. The method according to claim 1, wherein the non-contact distance acquiring device is an ultrasonic transducer.

10. The method according to claim 1, wherein the non-contact distance acquiring device is attached to the surgical instrument.

11. The method according to claim 1, wherein the non-contact distance acquiring device is at a remote location from the surgical instrument.

12. The method according to claim 4, wherein said imaging detector is selected from a group consisting of a digital camera, a MRI, a CT scanner, an X-ray scanner, a PET scanner, or an ultrasonic scanner.

13. The method according to claim 1, wherein said visual display is a digital display, a heads-up display, a monitor, a navigation instrument display or a microscope display.

14. The method according to claim 1, wherein at least one distance threshold is programmable into the computer such that when the distance between the surgical instrument and the object reduces below or reaches the at least one distance threshold, an alert is triggered.

15. The method according to claim 14, wherein the alert is a visual alert, an audio alert or a tactile alert.

16. The method according to claim 1 further comprising displaying the depth of the object in the surgical area of interest in the direction of the trajectory of the surgical instrument.

* * * * *